(12) United States Patent
Kachooei et al.

(10) Patent No.: US 10,314,618 B2
(45) Date of Patent: Jun. 11, 2019

(54) SYSTEM AND METHOD FOR AN EXTERNAL HIP FIXATOR

(71) Applicant: THE GENERAL HOSPITAL CORPORATION, Boston, MA (US)

(72) Inventors: Amir Kachooei, Boston, MA (US); Ali Moradi, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/328,632

(22) PCT Filed: Jul. 24, 2015

(86) PCT No.: PCT/US2015/041926
§ 371 (c)(1),
(2) Date: Jan. 24, 2017

(87) PCT Pub. No.: WO2016/014911
PCT Pub. Date: Jan. 28, 2016

(65) Prior Publication Data
US 2017/0209177 A1   Jul. 27, 2017

Related U.S. Application Data

(60) Provisional application No. 62/029,027, filed on Jul. 25, 2014.

(51) Int. Cl.
*A61B 17/64* (2006.01)

(52) U.S. Cl.
CPC ...... *A61B 17/6458* (2013.01); *A61B 17/6416* (2013.01)

(58) Field of Classification Search
CPC .............. A61B 17/748; A61B 17/6458; A61B 17/6416
See application file for complete search history.

(56) References Cited

U.S. PATENT DOCUMENTS

31,809 A * 3/1861 LaFaucheux ............. F41A 5/16
42/10
2,391,537 A * 12/1945 Anderson .............. A61B 17/66
606/59
(Continued)

FOREIGN PATENT DOCUMENTS

DE   3722595 A1   1/1989
EP   0011258 A1   5/1980
(Continued)

OTHER PUBLICATIONS

Biomet, VHS Hip Screw System, Product Information, http://www.biomet.com/trauma/products.cfm?pdid=4&majcid=29&prodid=116, accessed Jun. 26, 2014, 2 pages.
(Continued)

*Primary Examiner* — Jan Christopher L Merene
(74) *Attorney, Agent, or Firm* — Quarles & Brady LLP

(57) ABSTRACT

Embodiments of the invention provide a fracture fixation device and method for treatment of a bone fracture. The fracture fixation device includes a main body having a recess formed therein, and a compression element is configured to be received in the recess. The compression element has a passage dimensioned to receive a fracture fixation pin. A compressive force is generated across the bone fracture upon the compression element receiving the fracture fixation pin to promote healing of the bone fracture. The fracture fixation device is an external fixator that provides adjustable aspects of compression, rotation, and length in a simple design that facilitates bone healing by compression.

29 Claims, 8 Drawing Sheets

(56) References Cited

U.S. PATENT DOCUMENTS

| | | | | |
|---|---|---|---|---|
| 4,312,336 A * | 1/1982 | Danieletto | | A61B 17/6458 403/137 |
| RE31,809 E | 1/1985 | Danieletto et al. | | |
| 4,554,915 A * | 11/1985 | Brumfield | | A61B 17/6425 606/54 |
| 4,621,627 A * | 11/1986 | DeBastiani | | A61B 17/66 606/57 |
| 4,643,177 A * | 2/1987 | Sheppard | | A61F 13/041 602/40 |
| 4,988,349 A * | 1/1991 | Pennig | | A61B 17/6416 606/57 |
| 5,019,077 A * | 5/1991 | De Bastiani | | A61B 17/6416 606/54 |
| 5,127,914 A * | 7/1992 | Calderale | | A61B 17/746 606/65 |
| 5,292,322 A * | 3/1994 | Faccioli | | A61B 17/6458 606/53 |
| 5,304,177 A * | 4/1994 | Pennig | | A61B 17/6416 403/374.3 |
| 5,320,622 A * | 6/1994 | Faccioli | | A61B 17/6491 606/58 |
| 5,342,360 A | 8/1994 | Faccioli et al. | | |
| 5,454,810 A * | 10/1995 | Pohl | | A61B 17/6466 606/54 |
| 5,591,164 A * | 1/1997 | Nazre | | A61B 17/6491 606/54 |
| 5,728,096 A * | 3/1998 | Faccioli | | A61B 17/60 606/54 |
| 5,951,556 A * | 9/1999 | Faccioli | | A61B 17/6458 606/64 |
| 6,053,915 A * | 4/2000 | Bruchmann | | A61B 17/6416 606/54 |
| 6,409,729 B1 * | 6/2002 | Martinelli | | A61B 17/6466 606/59 |
| 6,500,177 B1 * | 12/2002 | Martinelli | | A61B 17/6458 606/54 |
| 6,709,433 B1 * | 3/2004 | Schoenefeld | | A61B 17/6425 606/54 |
| 6,840,939 B2 * | 1/2005 | Venturini | | A61B 17/6458 606/54 |
| 7,147,639 B2 * | 12/2006 | Berki | | A61B 17/6491 606/57 |
| 7,261,713 B2 * | 8/2007 | Langmaid | | A61B 17/6416 606/59 |
| 7,282,052 B2 * | 10/2007 | Mullaney | | A61B 17/6458 606/59 |
| 7,507,240 B2 * | 3/2009 | Olsen | | A61B 17/6416 606/57 |
| 7,544,208 B1 * | 6/2009 | Mueller | | A61F 2/44 623/17.15 |
| 7,575,575 B2 | 8/2009 | Olsen et al. | | |
| 7,588,571 B2 | 9/2009 | Olsen | | |
| 7,645,279 B1 * | 1/2010 | Haupt | | A61B 17/8625 606/54 |
| 7,731,738 B2 * | 6/2010 | Jackson | | A61B 17/8635 606/300 |
| 7,828,801 B2 * | 11/2010 | Mirza | | A61B 17/6416 606/54 |
| 7,846,162 B2 * | 12/2010 | Nelson | | A61B 17/7208 606/62 |
| 7,909,825 B2 * | 3/2011 | Saravia | | A61B 17/1725 606/63 |
| 7,914,533 B2 | 3/2011 | Nelson et al. | | |
| 7,918,876 B2 * | 4/2011 | Mueller | | A61F 2/44 606/250 |
| 7,942,875 B2 | 5/2011 | Nelson et al. | | |
| 7,981,116 B2 * | 7/2011 | Reeder, Jr. | | A61B 17/8872 606/104 |
| 8,057,473 B2 * | 11/2011 | Orsak | | A61B 17/60 606/55 |
| 8,147,491 B2 * | 4/2012 | Lavi | | A61B 17/6458 606/54 |
| 8,182,483 B2 | 5/2012 | Bagnasco et al. | | |
| 8,211,108 B2 * | 7/2012 | Matityahu | | A61B 17/1725 606/62 |
| 8,262,656 B2 * | 9/2012 | Mirza | | A61B 17/6416 606/54 |
| 8,287,538 B2 * | 10/2012 | Brenzel | | A61B 17/7225 606/62 |
| 8,287,539 B2 | 10/2012 | Nelson et al. | | |
| 8,287,541 B2 * | 10/2012 | Nelson | | A61B 17/1717 606/62 |
| 8,313,515 B2 * | 11/2012 | Brennan | | A61B 17/7005 606/256 |
| 8,366,710 B2 * | 2/2013 | Hirata | | A61B 17/6416 606/57 |
| 8,382,757 B1 | 2/2013 | Langmaid et al. | | |
| 8,388,619 B2 | 3/2013 | Mullaney | | |
| 8,419,732 B2 * | 4/2013 | Mullaney | | A61B 17/6458 606/54 |
| 8,439,917 B2 | 5/2013 | Saravia et al. | | |
| 8,460,294 B2 * | 6/2013 | Overes | | A61B 17/7241 606/62 |
| 8,518,039 B2 | 8/2013 | Mirza et al. | | |
| 8,585,702 B2 | 11/2013 | Orsak et al. | | |
| 8,721,566 B2 | 5/2014 | Connor et al. | | |
| 8,758,343 B2 * | 6/2014 | Maughan | | A61B 17/6466 606/54 |
| 9,763,710 B2 * | 9/2017 | Orsak | | A61B 17/746 |
| 2004/0193156 A1 * | 9/2004 | Waisman | | A61B 17/645 606/60 |
| 2005/0010224 A1 * | 1/2005 | Watkins | | A61B 17/746 606/65 |
| 2006/0229605 A1 * | 10/2006 | Olsen | | A61B 17/6416 606/54 |
| 2007/0100343 A1 * | 5/2007 | Cole | | A61B 17/72 606/67 |
| 2007/0255280 A1 * | 11/2007 | Austin | | A61B 17/6416 606/54 |
| 2008/0077142 A1 * | 3/2008 | James | | A61B 17/72 606/281 |
| 2008/0086136 A1 * | 4/2008 | Bednar | | A61B 17/746 606/266 |
| 2008/0269751 A1 * | 10/2008 | Matityahu | | A61B 17/1725 606/64 |
| 2008/0281326 A1 * | 11/2008 | Watanabe | | A61B 17/164 606/62 |
| 2010/0063550 A1 * | 3/2010 | Felix | | A61B 17/7032 606/301 |
| 2010/0217329 A1 * | 8/2010 | Brown | | A61B 17/742 606/301 |
| 2010/0222778 A1 * | 9/2010 | Bagnasco | | A61B 17/6483 606/58 |
| 2012/0123301 A1 * | 5/2012 | Connor | | A61B 17/70 600/594 |

FOREIGN PATENT DOCUMENTS

| | | |
|---|---|---|
| NL | 8802463 A | 5/1990 |
| WO | 8909031 A1 | 10/1989 |
| WO | 9007305 A1 | 7/1990 |
| WO | 9111150 A1 | 8/1991 |
| WO | 9111151 A1 | 8/1991 |
| WO | 9423662 A2 | 10/1994 |
| WO | 02094112 A1 | 11/2002 |

OTHER PUBLICATIONS

Depuy International Ltd., ATN Trochanteric Nail Surgical Technique, Issued Jan. 2005, 30 pages.

Johns Hopkins Medicine, "Fixing Hip Fractures" by Simon Mears, MD., http://www.hopkinsmedicine.org/gec/series/fixing_hip_fractures, Accessed Jun. 26, 2014.

ODI Orthopedic Designs, Inc., Talon Compression Hip Screw System, Surgical Technique Manual, Copyright 2001 Orthopedic Designs, Inc., Revision B, 12 pages.

Orthofix, Inc., Goffried Percutaneous Compression Plating for Pertrochanteric Hip Fractures, Copyright Jun. 2003, 4 pages.

(56) References Cited

OTHER PUBLICATIONS

Smith & Nephew, ACCORD Cable System, Surgical Technique, May 2008, 16 pages.
Smith & Nephew, IMHS CP Clinically Proven Intramedullary Hip Screw, Copyright 2012, 36 pages.
Smith & Nephew, PERI-LOC PFP, 4.5mm Proximal Femur Locking Plate, Nov. 2008, 34 pages.
Smith & Nephew, TRIGEN Intramedullary Nail System, Copyright 2012-2013 Smith & Nephew Inc., REVA Jan. 2013, 12 pages.
Stryker, Gamma3(TM) The Compact Titanium Version of the Gamma(TM) Nail System, Copyright 2005 Stryker, 6 pages.
Stryker, Why One Million Gamma(TM) Nails Have Been Implanted Worldwide, Copyright 2006 Stryker, 2 pages.
Swemac, Medoff Sliding Plate, Oct. 23, 2013, 28 pages.
Synthes, PFNA. Proximal Femoral Nail Antirotation, Technique Guide, Version AC Rev. 1, Dec. 2011.
Synthes, Titanium Trochanteric Fixation Nail System. For Intramedullary Fixation of Proximal Femur Fractures. Technique Guide, Copyright 2002 Synthes, Inc., 68 pages.
Synthes, Universal Locking Trochanter Stabilization Plate (ULTSP). For Use with the DHS/DCS and LCP DHHS Systems, Copyright 2007 Synthes Inc., 17 pages.
PCT International Search Report and Written Opinion, PCT/US2015/041926, dated Oct. 15, 2015.

* cited by examiner

SYSTEM AND METHOD FOR AN EXTERNAL HIP FIXATOR

CROSS-REFERENCE TO RELATED APPLICATIONS

This application represents the U.S. National Stage of International Application No. PCT/US2015/041926, filed Jul. 24, 2015 which claims priority from U.S. Patent Application No. 62/029,027 filed Jul. 25, 2014. The contents of this application are hereby incorporated by reference as if set forth in their entirety herein.

STATEMENT REGARDING FEDERALLY SPONSORED RESEARCH

Not applicable.

FIELD OF THE INVENTION

The present invention relates to a fracture fixation device for treatment of a bone fracture. More specifically, the present invention relates to an external fracture fixation device for intertrochanteric fractures.

BACKGROUND OF THE INVENTION

Approximately 252,000 hip fractures occur each year in the United States. Despite the relatively small incidence, hip fractures are responsible for approximately 3.5 million hospital days in the United States. In addition, hip fractures account for more hospital days than tibia fractures, vertebral fractures, and pelvic fractures combined. Further, hip fractures account for more than half of the total hospital admissions of all fractures and more than half of the ambulance calls for fractures.

Various types of orthopedic devices are known for the fixation of bone fragments. Such devices typically are used to stabilize bones by maintaining fractured bone portions in relatively fixed positions with respect to each other. The alignment and stability provided by the devices promotes the healing of fractures, allowing proper fusion to occur.

Internal fixation devices include bone screws, which are used in a variety of orthopedic applications for fixation of bone fragments. Bone fragments may be positioned in a desired configuration, and one or more holes may be drilled and tapped across the fracture. Compression and stabilization of the bone fragments may then be effected by screwing bone screws into the holes. One limitation associated with bone screws, however, is that repositioning or adjusting the bone screws following implantation is difficult. In order to accommodate a different alignment, it is often necessary to remove the original bone screws and drill new holes for subsequent bone screw implantation.

Metal pins also are often used to stabilize bones. Similar to bone screws, metal pins may be inserted in holes drilled across bone fragments to confer stability to the bone. However, as with bone screws, removal of the pins may be required if subsequent realignment of bone portions is necessary.

Intramedullary implants are another device used for fixation of bone fragments. Such a device may be placed in the central canal of a fractured bone and locked thereto at the longitudinal ends of the device using screws. The use of intramedullary implants is very invasive, though, and the implants are difficult to manipulate once installed within the canals of bone fragments. In the case of intertrochanteric hip fractures, intramedullary nails interlock proximally into the femoral head. However, often times, patients managed with intramedullary nailing experience increased pain and deformity, compared to patients managed with plate fixation. In addition, patients managed with intramedullary nailing often have more procedure-related complications, particularly bone fracture.

External fixation devices also are commonly used to stabilize bone segments. These devices employ a plurality of pins which extend through a patient's skin into holes drilled in fractured bone. Clamps are used to secure the pins to a common apparatus, which may, for example, take the form of a rod that is disposed generally parallel to the anatomically correct longitudinal axis of the fractured bone. The clamps in combination with the common apparatus create a rigid frame for immobilizing the fracture to promote healing.

External skeletal fixation is a preferred method of treatment for various limb deformities, injuries, and other conditions including: severe open fractures, fractures associated with severe burns, fractures requiring distraction, fractures requiring limb lengthening, arthrodesis, infected fractures, and nonunions. External fixation offers several advantages over the above-mentioned internal fixation approaches. For example, external fixation enables skeletal stabilization to be managed from a location that is generally remote from the proximity of deformity, injury, or disease, thereby permitting direct surveillance of the limb and wound during related or subsequent procedures. In addition, external fixation facilitates adjustment of fracture alignment, bone lengthening, bone compression, and fixed distraction following initial surgery. Furthermore, minimal interference with proximal and distal joints allows immediate mobilization of a wounded limb, and insertion of the fixator pins can be performed under local anesthesia.

However, external fixation is not commonly considered for the treatment of intertrochanteric femur fractures. An intertrochanteric hip fracture occurs between the greater trochanter and the lesser trochanter. Conventionally, intertrochanteric fractures are treated using an engineered metallic fixation device designed to maintain the fracture fragments in their post reduction position. Compression across the fracture site compresses the proximal and distal fragments to each other, which assists in the healing of the fracture.

The current treatment of intertrochanteric fractures is surgical intervention. Though healing rates for previous nonsurgical methods may have been acceptable, these nonsurgical methods are often accompanied by unacceptable morbidity and mortality rates due to frequent, non-orthopedic complications associated with prolonged immobilization or inactivity. The complications include the following: 1) pulmonary complications of pneumonia resulting from inactivity, 2) pulmonary emboli from deep vein thrombosis (DVT) caused by immobilization of an extremity, 3) bedsores from prolonged bed rest, 4) loss of motion of the lower extremity joints and muscle atrophy due to prolonged immobilization, and 5) union of the fracture in an unacceptable position resulting in a deformity.

Early experiences with external fixation for intertrochanteric fractures were associated with postoperative complications, such as varus collapse. However, the ability to treat intertrochanteric fractures with short operative times, minimal blood loss, and potentially with only local anesthesia have led some to advocate its use in selected patients. The patients most suitable for such treatment include those at unacceptably high risk for complications related to general or regional anesthesia. The device typically consists of one or two half pins placed into the femoral neck to within 10 millimeters of the subchondral bone. The fracture is reduced and the pins are connected through clamps and a bar to two or three half pins placed in the proximal femur.

Since the elderly population is mostly affected with intertrochanteric fractures, expedition in mobilization with less invasive surgeries, lighter anesthesia, less blood loss, and smaller incisions are desirable for the fracture fixation techniques. The future of intertrochanteric fracture repair focuses, in part, on fixation devices that are more forgiving, with retention of the fixation, regardless of whether the fracture is ideally reduced or has an element of instability.

While various surgical fixation devices are now available for the treatment of essentially all intertrochanteric fractures, the indications and contraindications of the technique must also be matched with the patient's activity level, degree of osteoporosis, and realistic expected outcome. In addition, there remains a need for fixation devices with improved adjustability. In particular, there remains a need for fixation devices with improved joints and overall constructions.

Therefore, a fracture fixation device is needed that overcomes the above limitations.

SUMMARY OF THE INVENTION

The present invention relates to a fracture fixation device for treatment of a bone fracture. In some embodiments, the fracture fixation device is for treatment of intertrochanteric fractures. Unlike conventional treatment for intertrochanteric fractures, which typically uses open reduction and internal fixation done by dynamic hip screws (DHS), the fracture fixation device is an external fixator that is still capable of applying dynamic compression at the fracture site to help fracture healing. In addition, the present fracture fixation device provides adjustable aspects of compression, rotation, and length in a simple design that is low in price and lightweight, while still facilitating bone healing by compression.

Some embodiments of the invention provide a fracture fixation device for treatment of a bone fracture. The fracture fixation device includes a main body having a recess formed therein, and a compression element is configured to be received in the recess. The compression element has a passage dimensioned to receive a fracture fixation pin. A compressive force is generated across the bone fracture upon the compression element receiving the fracture fixation pin to promote healing of the bone fracture.

In some embodiments, the main body and compression element are configured to remain external to a subject when the fracture fixation device is coupled to the subject during treatment of the bone fracture. The main body can be constructed from a material including an aluminum alloy, a stainless steel material, a carbon fiber material or a compact plastic material. In one embodiment, the material is partially radiolucent.

The recess of the main body, in some embodiments, is substantially oval in cross-section. Similarly, the compression element includes an oval in cross-section shape dimensioned to be received by the substantially oval shaped recess. The compression element may include an opening substantially parallel to the passage, and the opening may be dimensioned to receive a compression adjustment screw for adjusting the compressive force generated across the bone fracture. In some embodiments, the compression adjustment screw includes external threads configured to engage internal threads of the opening. As such, upon rotation of the compression adjustment screw, the compression element translates within the recess of the main body.

In yet other embodiments, the compression element includes a guide channel extending through a peripheral portion of the compression element. The guide channel may be configured to receive a locking pin extending through a top portion of the main body to inhibit translation of the compression element within the recess.

In one embodiment, the main body of the fracture fixation device includes a first section including the recess and compression element, and a second section pivotally coupled to the first section by a first connection. The first connection allows the first section and the second section to pivot relative to each other about a first axis that is transverse to the passage of the compression element. In some embodiments, the first connection is formed by a first connection bolt extending through the first section and the second section along the first axis.

The compression element may further comprises an additional passage that is substantially parallel to the passage and is dimensioned to receive an additional fracture fixation pin. The fracture fixation pin and the additional fracture fixation pin are configured to be received by a femoral neck at a predetermined angle relative a femoral shaft. The predetermined angle may be in the range of 110 degrees to 160 degrees and is adjustable by pivoting the first section about the first axis. The fracture fixation pin and the additional fracture fixation pin may extend across a fracture line created by the bone fracture, which may include, for example, an intertrochanteric hip fracture where the fracture line extends from a greater trochanter to a lesser trochanter of a femur.

The main body of the fracture fixation device may further include a third section coupled to the second section by a second connection. The second connection allows the second section and the third section to pivot relative to each other about a second axis that is longitudinal to the passage of the compression element. The second connection may further allow the second section and the third section to axially translate along the second axis to either increase or decrease an overall length of the fracture fixation device. In some embodiments, the second connection is formed by a substantially cylindrical pivot pin extending along the second axis and positioned substantially perpendicular to the first connection bolt.

In some embodiments, the main body of the fracture fixation device may further include a fourth section coupled to the third section by a third connection. The third connection is formed by a third connection bolt extending through the third section and the fourth section along the third axis. The third connection bolt is positioned substantially perpendicular the pivot pin of the second connection. The third connection may allow the third section and the fourth section to pivot relative to each other about a third axis that is transverse to the passage of the compression element. As such, the first connection, the second connection, and the third connection may be adjustable to allow the fracture fixation device to be externally coupled to a bone of a subject.

In yet other embodiments, the main body of the fracture fixation device may include a fifth section releasably coupled to the fourth section, such that the fourth section and the fifth section are opposed sections dimensioned to create one or more openings configured to receive a bone fixation pin. One or more clamping bolts may extend through the fourth section and the fifth section, wherein upon rotation in a first direction of the clamping bolt, the bone fixation pin is clamped within the opening. In some embodiments, an additional bone fixation pin may be received by one or more additional openings created by the opposing fourth section and fifth section of the main body. The bone fixation pin and the additional bone fixation pin may be configured to be received by a femoral shaft. In some embodiments, the distance between the at least one opening and the at least one additional opening is between about 0.5 centimeters and about 2.5 centimeters.

Other embodiments of the invention provide a method for treatment of a bone fracture using a fracture fixation device. The method includes adjusting a compression element configured to be received in a recess formed in a main body. A fracture fixation pin is inserted through a passage created within the compression element and into a bone containing the bone fracture. A compressive force is generated across the bone fracture to promote healing of the bone fracture.

In some embodiments, the method includes coupling the fracture fixation device external to a subject during treatment of the bone fracture. In addition, a compression adjustment screw may be inserted into an opening of the compression element. The compression adjustment screw may be rotated to translate the compression element within the recess of the main body, thereby adjusting the compressive force generated across the bone fracture.

In some embodiments, a first section of the main body may be pivoted relative to a second section of the main body about a first axis and fixated in a first position. The first axis may be transverse to the passage of the compression element. In addition, the second section may be pivoted relative to a third section of the main body about a second axis and fixated in a second position. The second axis may be longitudinal to the passage of the compression element. The second section and the third section may be axially translated along the second axis to increase or decrease an overall length of the fracture fixation device. In addition, the third section may be pivoted relative to a fourth section of the main body about a third axis and fixated in a third position. The third axis may be transverse to the passage of the compression element. Thus, pivoting sections of the main body about the first axis, the second axis, or the third axis and fixating in the first position, second position, or third position allow the fracture fixation device to be externally coupled to a bone of a subject.

These and other features, aspects, and advantages of the present invention will become better understood upon consideration of the following detailed description, drawings, and appended claims.

DETAILED DESCRIPTION OF THE INVENTION

Figure 1:
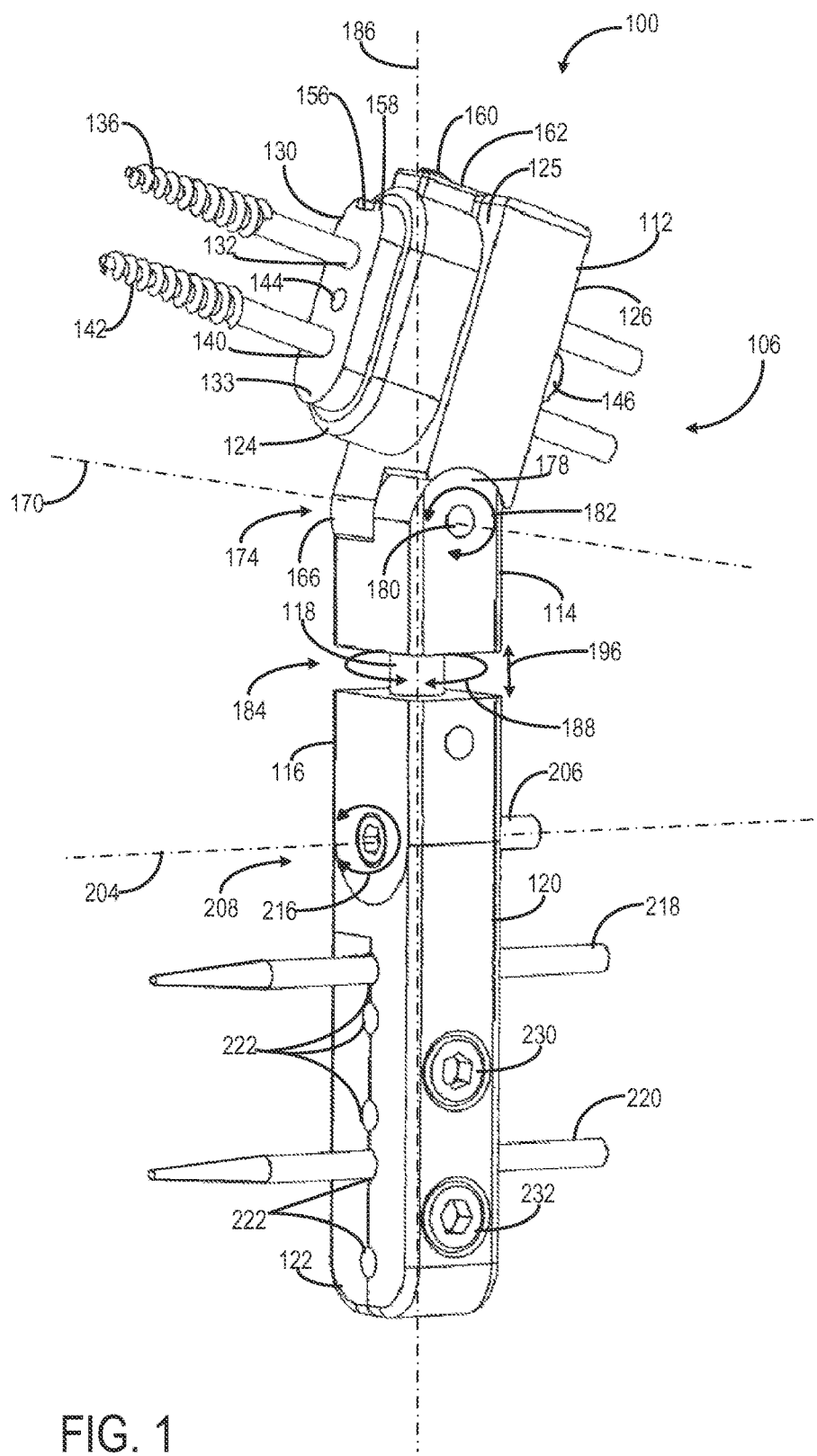
FIG. 1 is a perspective view of an example fracture fixation device according to one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Figure 9:
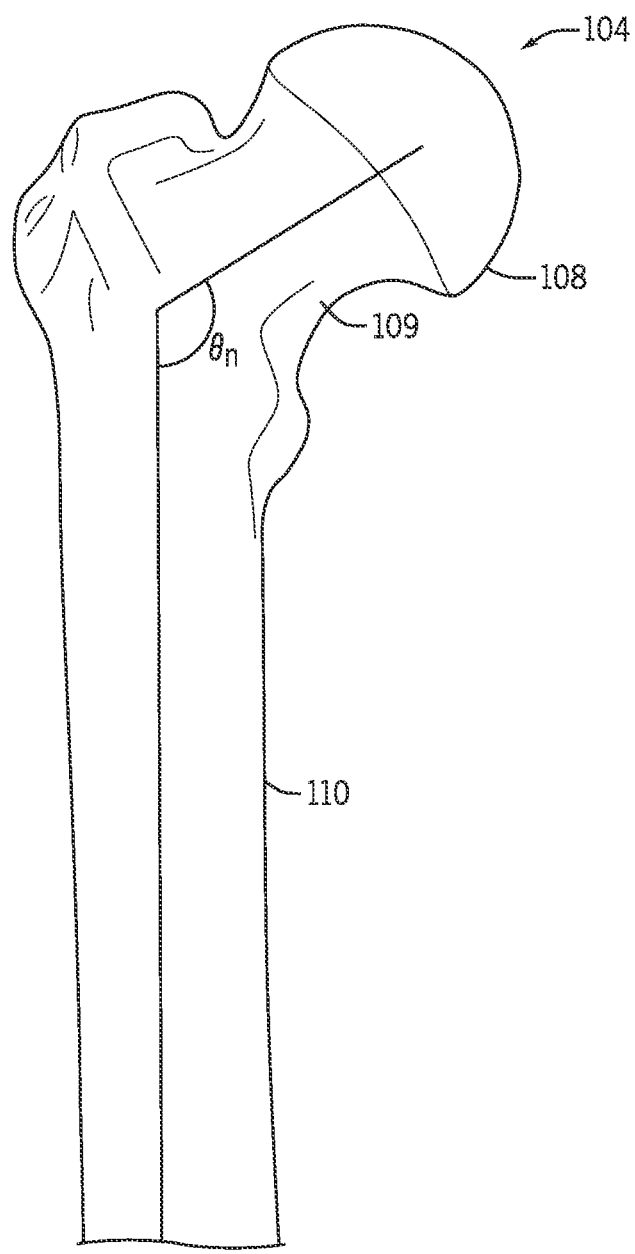
FIG. 9 is a side view of a femur bone including a femoral neck and a femoral shaft that create a femoral neck-shaft angle.
Figure 10:
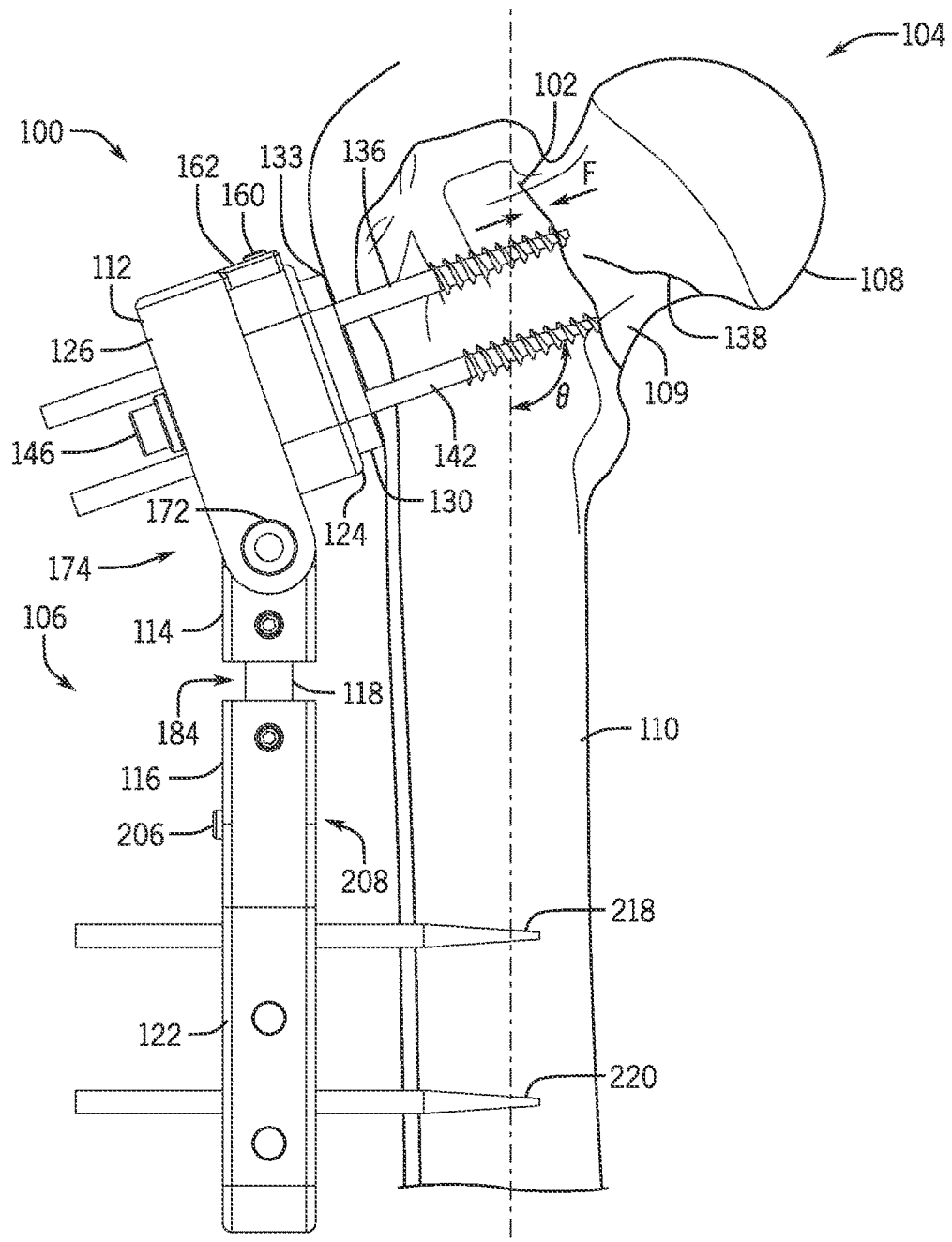
FIG. 10 is a side view of the femur bone of FIG. 9 including an intertrochanteric hip fracture and the fracture fixation device of FIG. 1 coupled to the femur bone.

FIG. 1 illustrates an example fracture fixation device 100 for treatment of a bone fracture. For example, the fracture fixation device 100 may be used externally, as shown in FIG. 10, to fix an intertrochanteric fracture 102 of a femur bone 104. The fracture fixation device 100 is formed by a main body 106. In some embodiments, the overall shape of the main body 106 can resemble a femoral head 108 and a femoral shaft 110 of a femur bone, such as the femur bone shown in FIGS. 9 and 10, so that the main body 106 can be externally attached to a patient. In some embodiments, the main body 106 of the fracture fixation device 100 can be constructed from an aluminum alloy material, a stainless steel material, a carbon fiber material, or a compact plastic material, for example. In some embodiments, the main body 106 of the fracture fixation device 100 can be constructed from a radiolucent material.

Returning to FIG. 1, the main body 106 can be formed by a first section 112 pivotally coupled to one end of a second section 114. An opposing end of the second section 114 may be releasably joined to one end of a third section 116 by a pivot pin 118 extending there between. An opposing end of the third section 116 may be pivotally coupled to one end of a fourth section 120, and a fifth section 122 may be coupled to a side portion of the fourth section 120. Thus, the sections 112, 114, 116, 120, and 122 are coupled to one another, as just described, to form the main body 106 of the fracture fixation device.

In the case where the fracture fixation device 100 is used for treatment of intertrochanteric fractures of the femur bone, the first section 112 is positioned proximally relative to the distal fourth and fifth sections 120, 122. However, it is contemplated that the fracture fixation device 100 may be used on other bone fractures within a patient, and thus the fracture fixation device 100 is not limited to treatment for intertrochanteric fractures. In one non-limiting example, the fracture fixation device 100 may be utilized for treatment of bone fractures of the basocervical neck of the femur, the proximal humerus head and neck, the metatarsal neck of the foot, the metacarpal neck of the hand, or the distal radius fracture of the wrist.

Figure 2:
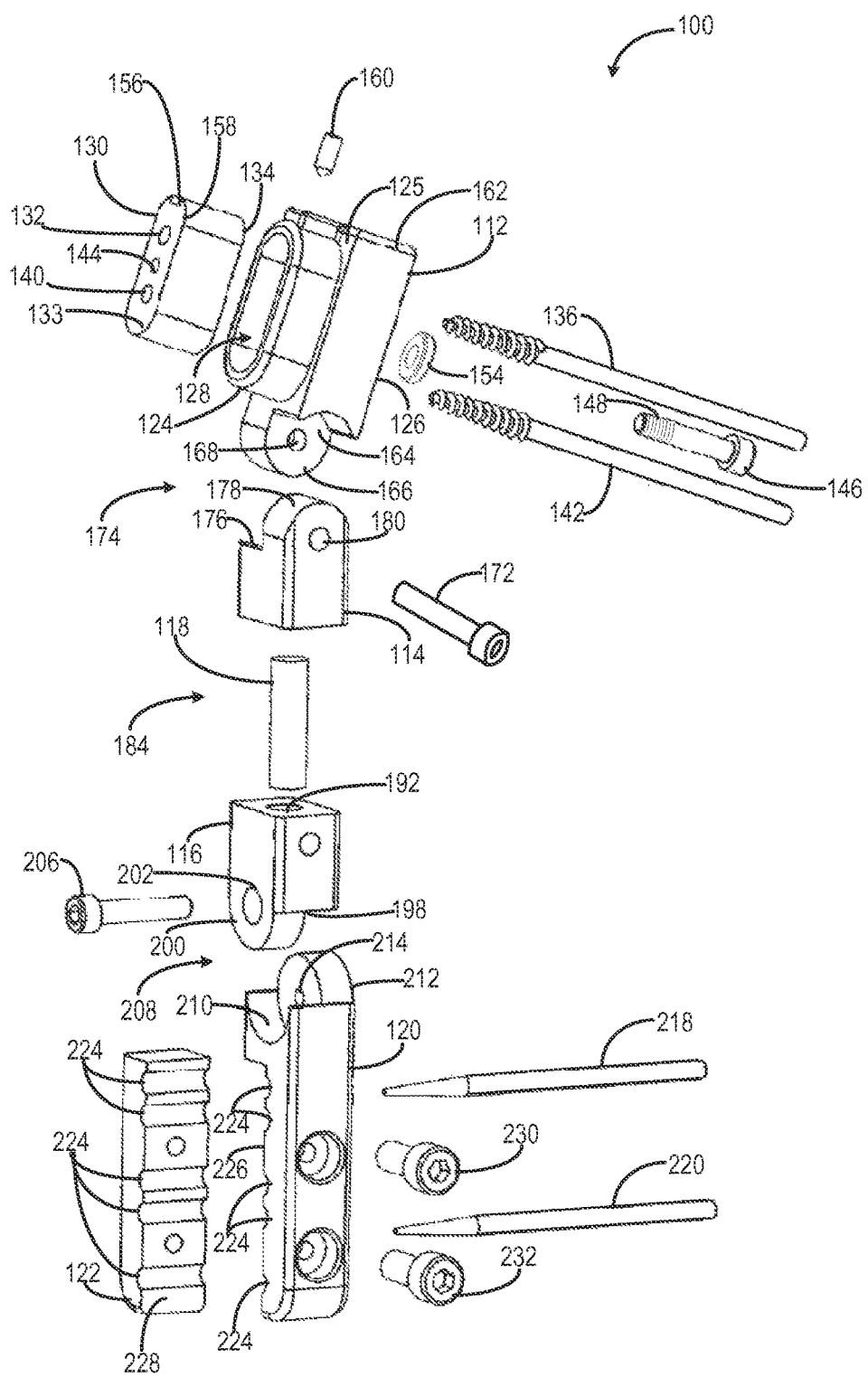
FIG. 2 is an exploded view of the fracture fixation device of FIG. 1.

Referring now to FIGS. 1 and 2, the first section 112 includes a substantially oval rib 124 outwardly extending from a front surface 125 of the first section 112. The oval rib 124 defines a recess 128 that may be configured to receive a compression element 130. Thus, the recess 128 and the compression element 130 are substantially oval in cross-section to allow the compression element 130 to be received by the recess 128. The term oval used to describe the shape of the various components (e.g., the rib 124, the recess 128, and the compression element 130) of the fracture fixation device 100 can be a shape that, in cross-section, resembles two circles joined by a rectangle. However, the shapes and/or cross-sections of the various components (e.g., the rib 124, the recess 128, and the compression element 130) of the fracture fixation device 100 can have any other suitable geometric shape and/or cross-section.

Figure 8:
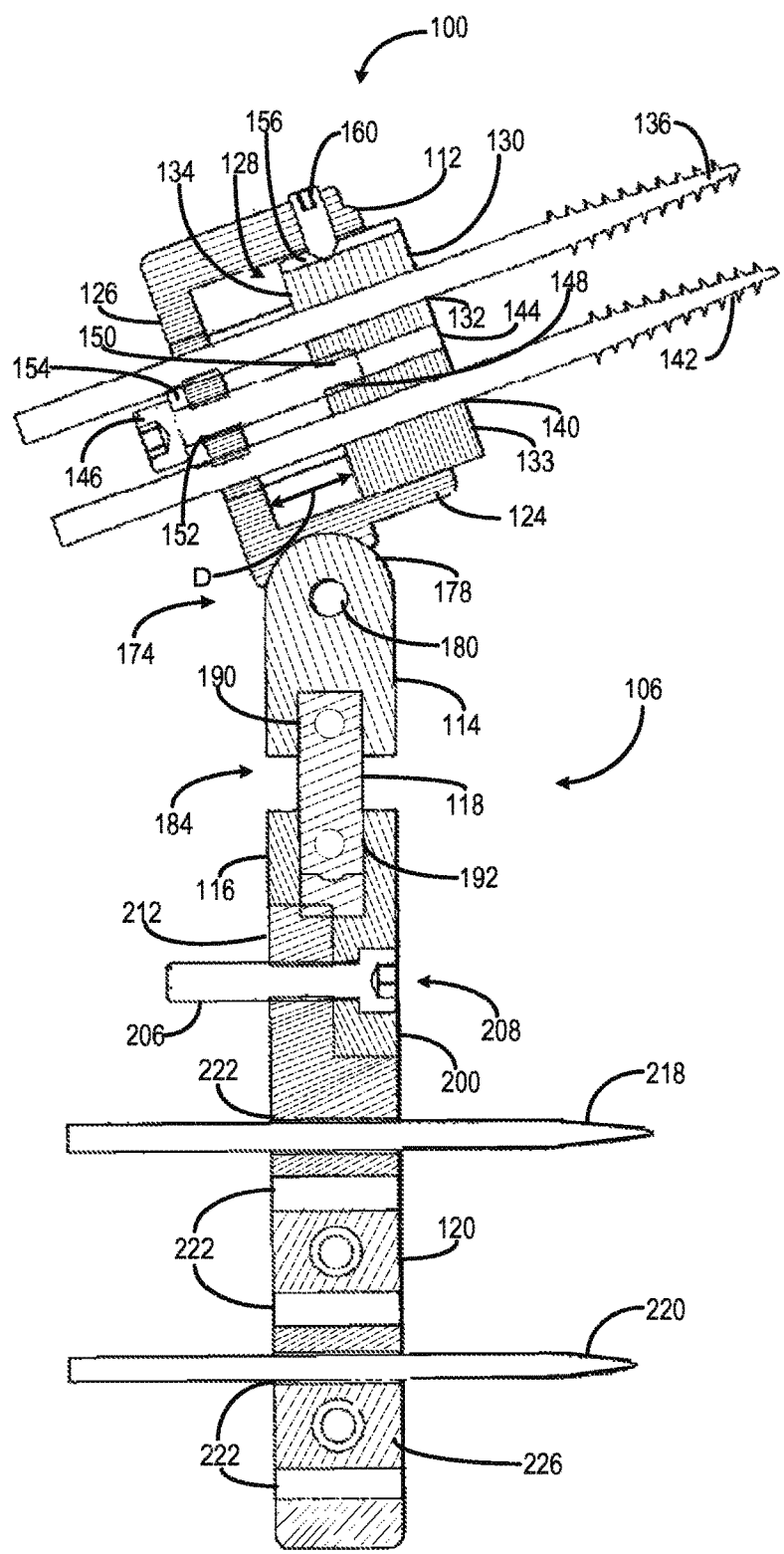
FIG. 8 is a cross-sectional view of the fracture fixation device of FIG. 1 taken along line 8-8 of FIG. 6.

The compression element 130 may include a passage 132 that extends from a front surface 133 to a rear surface 134 of the compression element 130, as best shown in the cross-sectional view of the fracture fixation device 100 in FIG. 8. The passage 132 may be dimensioned to receive a fracture fixation pin 136. The fracture fixation pin 136 may be, for example, a Schanz-type pin that is self drilling, or a standard Schanz pin that can be inserted after drilling into the femoral head 108 of the femur bone 106 (see FIGS. 9 and 10). A compressive force F, as shown in FIG. 10, may be generated across the bone fracture 102 upon the compression element 130 receiving the fracture fixation pin 136 to promote healing of the bone fracture. Thus, the compression element 130 can allow a proximal fracture fragment 138 to collapse back, and the compression force F can occur along the bone fracture 102 line for healing. This function may resemble internally fixed Dynamic Hip Screws (DHS), however, without requiring open reduction and internal fixation, as is commonly done by dynamic hip screws. Therefore, the fracture fixation device 100 is an external fixator that is still capable of applying dynamic compression at the fracture site to help fracture healing.

The compression element 130 may also include an additional passage 140 (see FIG. 8) that extends from the front surface 133 to the rear surface 134 of the compression element 130. The additional passage 140 may be substantially parallel to the passage 132 and may be dimensioned to receive an additional fracture fixation pin 142 to allow the proximal fracture fragment 138 to collapse back to provide the compression force F along the bone fracture 102 line for healing.

Returning to FIGS. 1 and 2, the compression element 130 can further include an opening 144 positioned between, and is substantially parallel to, the passage 132 and the additional passage 140. The opening 144 can extend from the front surface 133 to the rear surface 134 of the compression element 130, and the opening 144 may be dimensioned to receive a compression adjustment screw 146. The compression adjustment screw 146 may include external threads 148, as shown in FIG. 2, that are configured to engage internal threads 150 positioned on a surface of the opening 144 (see FIG. 8). The compression adjustment screw 146 may be inserted through a hole 152 that extends from a rear surface 126 of the first section 112 into the recess 128. Upon insertion of the compression element 130 into the recess 128, the external threads 148 of the compression adjustment screw 146 can engage the corresponding internal threads 150 within the opening 144 of the compression element 130, as shown in FIG. 8.

Upon rotation of the compression adjustment screw 146, the compression element 130 may translate within the recess 128 of the first section 112 of the main body 106 in order to adjust the compressive force F generated across the bone fracture 102 after insertion of the fracture fixation pins 136, 142. In addition, depending on the amount of rotation of the compression adjustment screw 146, the compression element 130 can slide back a predetermined distance D within the recess 128, as shown in FIG. 8. The predetermined distance D can be between about 0.5 centimeters to about 2.5 centimeters. Thus, as the compression element 130 translates within the recess 128, perhaps due to the force generated by the weight of the patient onto the fracture fixation device 100, the fracture fixation pins 136, 142 may also translate within the corresponding passages 132, 140.

Returning to FIG. 2, the compression adjustment screw 146 may be configured to receive a seating element 154, such as a washer, to seat the compression adjustment screw 146 on the rear surface 126 of the first section 112 and to further help prevent the compression adjustment screw 146 from sliding through the hole 152. In one non-limiting example, the compression adjustment screw may 146 may be a lag screw, however any suitable screw or fastener may be used.

Figure 7:
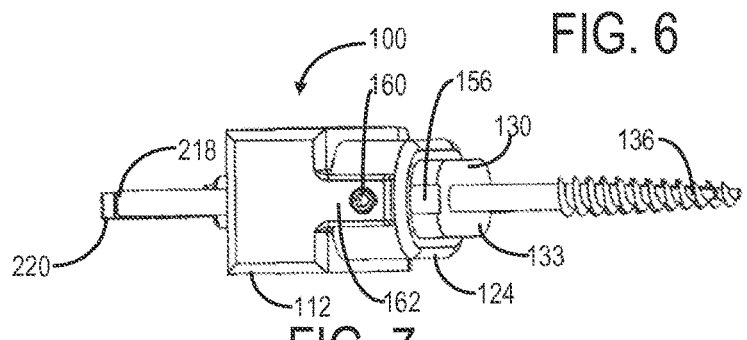
FIG. 7 is a top view of fracture fixation device of FIG. 1.

The compression element 130 may further include a guide channel 156, as best shown in FIGS. 1 and 8, that extends from the front surface 133 to the rear surface 134 of the compression element 130 along a peripheral portion 158 of the compression element 130. The guide channel 156 may be configured to receive a locking pin 160 that extends through a top portion 162 of the first section 112, as shown in FIG. 7. In some embodiments, the locking pin 160 may be tightened, and thus engage the guide channel 156, in order to lock, or inhibit translation of, the compression element 130 in place within the recess 128. In other embodiments, the locking pin 160 may extend into the guide channel 156, but not engage the guide channel 156, to allow the compression element 130 to translate with the recess 128.

Returning to FIG. 2, the first section 112 of the main body 106 further includes an arcuate cut-out portion 164 adjacent an arcuate member 166 downwardly extending from the first section 112. The arcuate member 166 may include an opening 168 that extends along a first axis 170, as shown in FIG. 1, and configured to receive a first connection bolt 172, as will be described in further detail below.

The main body 106 further includes the second section 114 that may be pivotally coupled to the first section 112 by a first connection 174, as shown in FIG. 1. Similar to the first section 112, the second section 114 may include an arcuate cut-out portion 176 adjacent an arcuate member 178 upwardly extending from the second section 112. The arcuate member 178 may include an opening 180 that extends along the first axis 170, as shown in FIG. 1, and configured to receive the first connection bolt 172 (see FIG. 4). The arcuate cut-out portion 164 of the first section 112 may be configured to receive the arcuate member 178 of the second section 114. Likewise, the arcuate cut-out portion 176 of the second section 114 may be configured to receive the arcuate member 166 of the first section 112. Therefore, the first connection 174 may be formed by the first connection bolt 172 extending through the openings 168, 180 of the arcuate members 166, 178 along the first axis 170.

Figure 3:
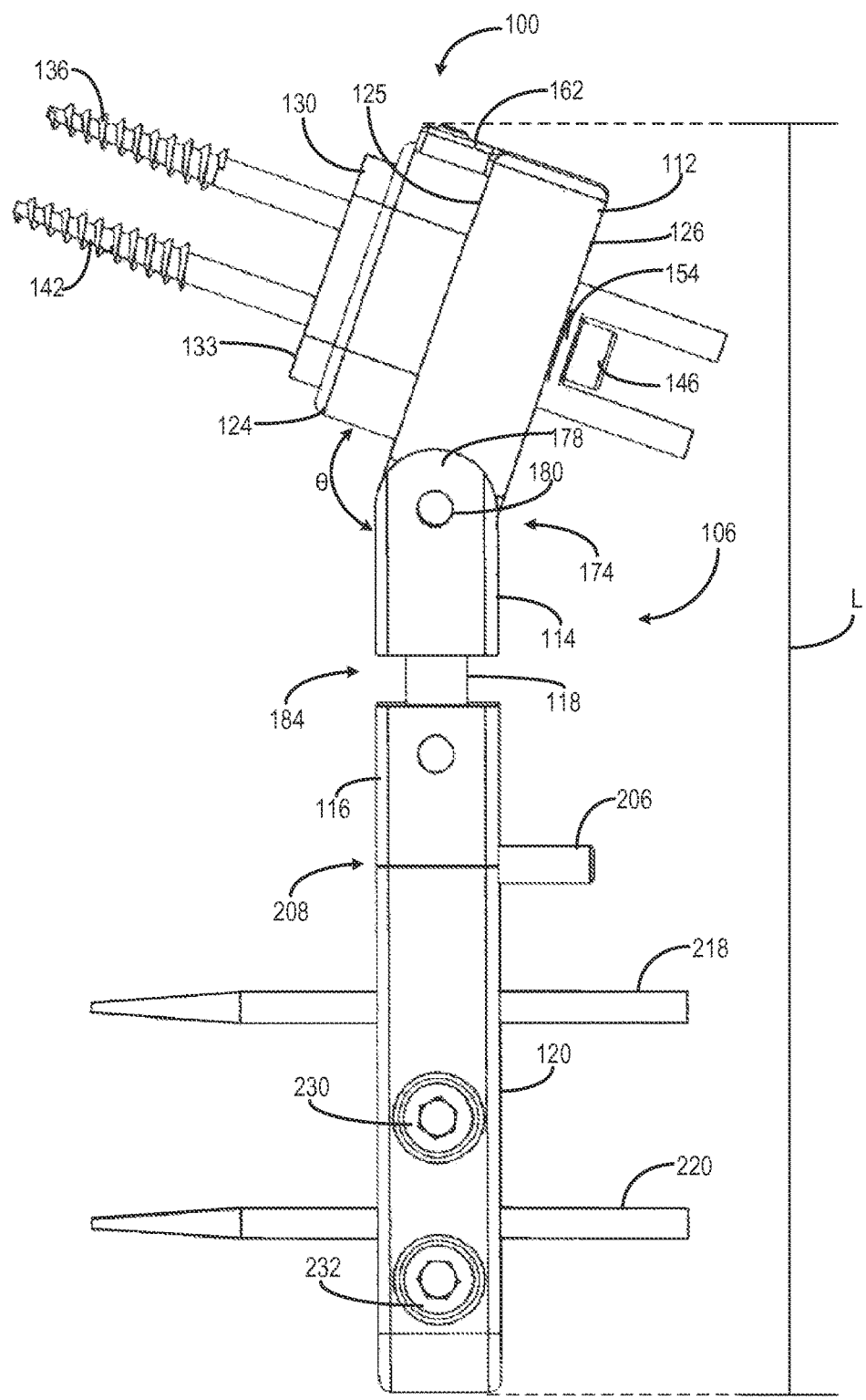
FIG. 3 is a left side view of the fracture fixation device of FIG. 1 showing a length dimension.
Figure 4:
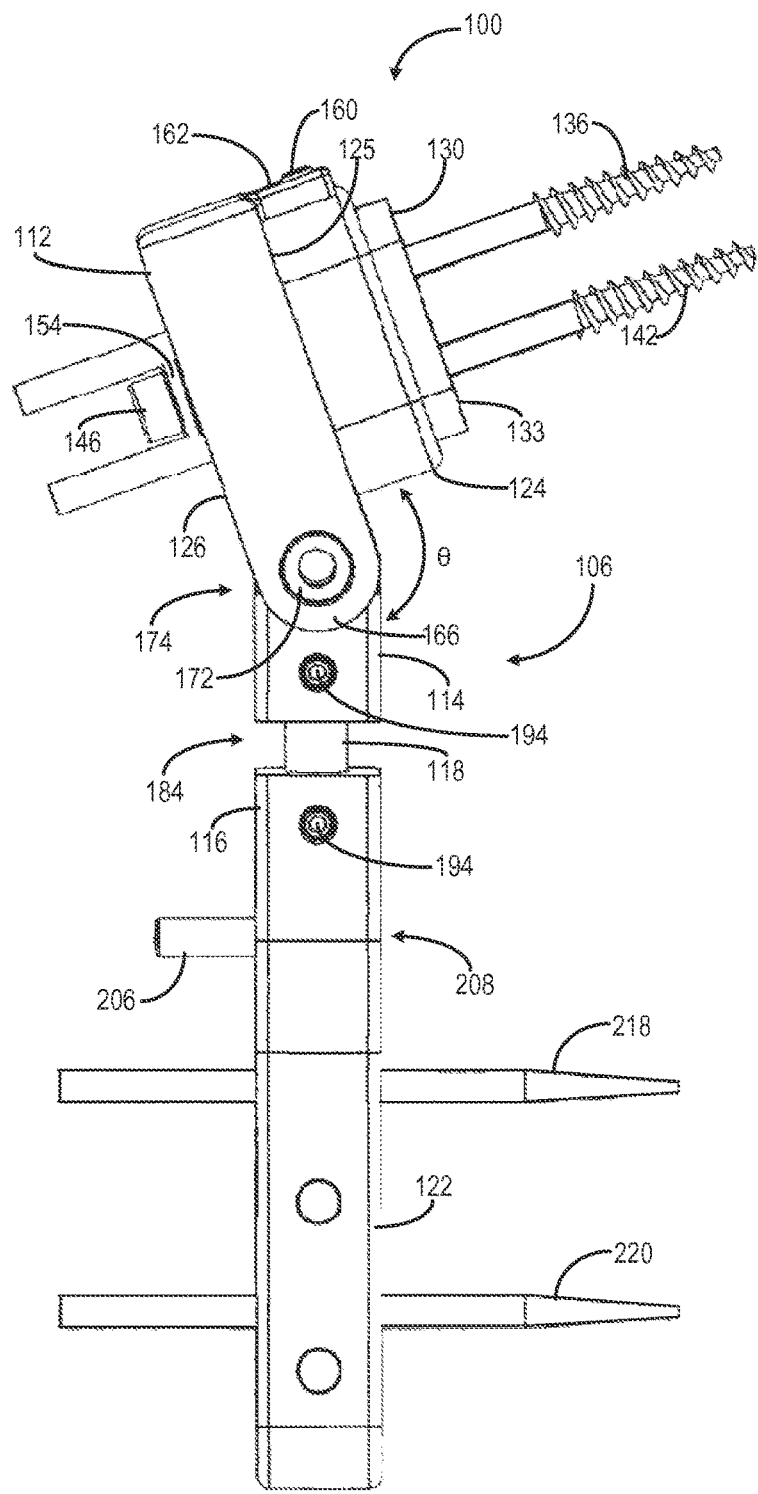
FIG. 4 is a right side view of the fracture fixation device of FIG. 1.

The first connection 174 can allow the first section 112 and the second section 114 to pivot relative to each other about the first axis 170 in the direction indicated by the arrow 182. The first axis 170 may be transverse to the passage 132 of the compression element 130. The pivotal movement in the direction of the arrow 182 may allow the first section 112 and the second section 114 to create an angle θ, as shown in FIGS. 3 and 4, that simulates a natural femoral neck-shaft angle $θ_n$, as shown in FIG. 9. Thus, as shown in FIG. 10, the fracture fixation pins 136, 142 may be configured to be received by a femoral neck 109 at a predetermined angle, namely angle θ, relative the femoral shaft 110 and extend across a fracture line created by the bone fracture 102 to treat an intertrochanteric hip fracture, for example. The predetermined angle θ created by the pivotal movement between the first section 112 and the second section 114 may be in the range of about 110 degrees to about 160 degrees.

Returning to FIGS. 1 and 2, the main body 106 of the fracture fixation device 100 may further include the third section 116 coupled to the second section 114 by a second connection 184. The second connection 184 may be formed by the substantially cylindrical pivot pin 118 that extends along a second axis 186 and is substantially perpendicular to the first connection bolt 172. The second axis 186, as shown in FIG. 1, is longitudinal to the passage 132 of the compression element 130. The second connection 184 can allow the second section 114 and the third section 116 to pivot relative to each other about the second axis 186 in the direction indicated by the arrow 188.

As best shown in FIG. 8, a first end of the pivot pin 118 may be received by a bore 190 of the second section 114. Similarly, an opposing end of the pivot pin 118 may be received by a bore 192 of the third section 116, thereby allowing the second section 114 and the third section 116 to pivot relative to each other about the second axis 186. Once the second section 114 and the third section 116 are pivoted to a desired position, perhaps to conform to the hip anatomy of the patient receiving the fracture fixation device, a pair of fasteners 194 may be inserted into the second section 114 and the third section 116, as shown in FIG. 4. Thus, the pair of fasteners 194 may engage the pivot pin 118 to maintain the pivotal position of the second section 114 relative to the third section 116, as well as maintain the connection between the second section 114 and the third section 116.

Returning to FIG. 1, the second connection 184 further allows the second section 114 and the third section 116 to axially translate along the second axis 186 in the direction indicated by arrow 196. This axial translation may allow an overall length L (see FIG. 3) of the fracture fixation device 100 to be adjusted for the various lengths of the femur bone 104 exhibited by different patients. In addition, the axial translation may allow the user to adjust the length L of the fracture fixation device 100 based on the location of the bone fracture 102 and the preferred site of pin placement. The length L of the fracture fixation device 100 can be shortened or lengthened by about 2 centimeters. Once the desired length L is set, the pair of fasteners 194 may be tightened to secure the length L of the fracture fixation device 100.

Returning to FIG. 2, the third section 116 of the main body 106 further includes an arcuate cut-out portion 198 adjacent an arcuate member 200 downwardly extending from the third section 116. The arcuate member 200 may include an opening 202 that extends along a third axis 204, as shown in FIG. 1, and configured to receive a third connection bolt 206, as will be described in further detail below.

Figure 5:
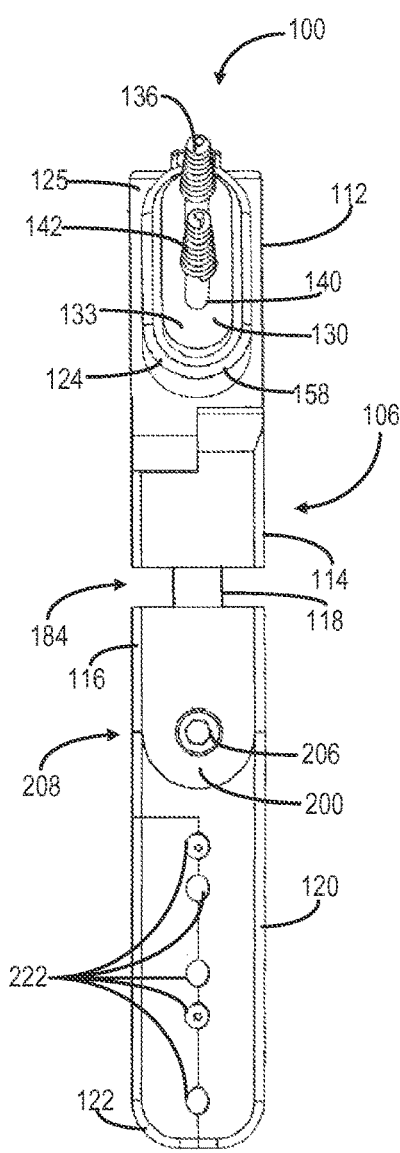
FIG. 5 is a front view of the fracture fixation device of FIG. 1.

The main body 106 further includes the fourth section 120 that may be pivotally coupled to the third section 116 by a third connection 208, as shown in FIG. 1. Similar to the third section 116, the fourth section 120 may include an arcuate cut-out portion 210 adjacent an arcuate member 212 upwardly extending from the fourth section 120. The arcuate member 212 may include an opening 214 that extends along the third axis 204, as shown in FIG. 1, and configured to receive the third connection bolt 206 (see FIG. 5). The arcuate cut-out portion 198 of the third section 116 may be configured to receive the arcuate member 212 of the fourth section 120. Likewise, the arcuate cut-out portion 210 of the fourth section 120 may be configured to receive the arcuate member 200 of the third section 116. Therefore, the third connection 208 may be formed by the third connection bolt 206 extending through the openings 202, 214 of the arcuate members 200, 212 along the third axis 204.

The third connection 208 can allow the third section 116 and the fourth section 120 to pivot relative to each other about the third axis 204 in the direction indicated by the arrow 216. The third axis 204 may be transverse to the passage 132 of the compression element 130. Thus, the third section 116 and the fourth section 120 can pivot with respect to each other in a sagittal plane to allow the user to adjust the plane of bone fixation pins 218, 220 in the femoral neck 109 with the bone fixation pins 218, 220 in the femoral shaft 110, as shown in FIG. 10.

Returning to FIGS. 1 and 2, the main body 106 of the fracture fixation device 100 further includes the fifth section 122 releasably coupled to the fourth section 120. The fourth section 120 and the fifth section 122 may be opposing sections dimensioned to create one or more openings 222 configured to receive the bone fixation pins 218, 220. The openings 222 may be created by corresponding semi-circular recesses 224 created on a first inner surface 226 and a second inner surface 228 of the fourth section 120 and the fifth section 122, respectively. Thus, when the fifth section 122 is aligned with the fourth section 120, the corresponding semi-circular recesses 224 on the first and second inner surfaces 226, 228 are aligned to create the openings 222.

Figure 6:
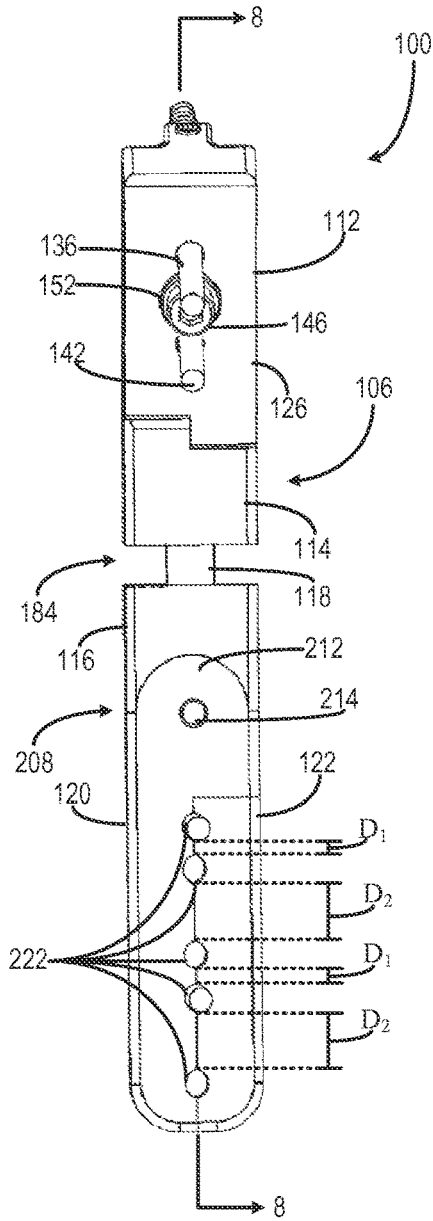
FIG. 6 is a rear view of the fracture fixation device of FIG. 1.

As depicted in FIG. 6, the fourth section 112 and the fifth section 122, when clamped together, comprise five openings 222 for placement of up to five bone fixation pins into the femoral shaft 110. Beginning at the upper-most opening 222, as shown in FIG. 6, the distance $D_1$ between the first and second, and third and forth openings are the same. The distance $D_1$ can be between about 0.5 centimeters and about 1.5 centimeters. The distance $D_2$ between the second and third openings 222, and the forth and fifth opening 222 are also the same. The distance $D_2$ can be between about 1.5 centimeters and about 2.5 centimeters. A fifth section (Shutter) is prepared on the backside of the fourth section that can be removed at the time of bone fixation pin placement so that it does not interfere with pin placement. It can be placed and tightened after the first pin is inserted into the femoral shaft and then the other pins can be inserted accordingly.

Once the bone fixation pins 218, 220 are positioned in the openings 222, a first clamping bolt 230 and a second clamping bolt 232, as shown in FIG. 1, may be inserted through receiving holes of the fourth and fifth sections 120, 122. Upon rotation of the clamping bolts 230, 232, the sections 120, 122 may be secured together and the bone fixation pins 218, 220 secured in place.

Turning now to FIGS. 9 and 10, during operation, the fracture fixation pins 136, 142 may be inserted into the femoral neck 109 of the femur bone 104 having the bone fracture 102. Similarly, the bone fixation pins 218, 220 may be inserted into the femoral shaft 110. The fracture fixation device 100 may then be coupled to the fracture fixation pins 136, 142 and the bone fixation pins 218, 220. More specifically, the passages 132, 140 of the compression element 130 may receive the fracture fixation pins 136, 142, and the openings 222 of the fourth and fifth sections 120, 122 may receive the bone fixation pins 218, 220. One or more of the connections 174, 184, 208 may be adjusted about the axes 170, 186, 204, respectively, to ensure proper security of the fracture fixation pins 136, 142 and bone fixation pins 218, 220. The corresponding fasteners (i.e., 146, 160, 172, 194, 206, 230, 232) may then be tightened to secure the sections 112, 114, 116, 120, 122 of the fracture fixation device 100 together.

The fracture fixation device 100 described includes several benefits over other currently available fixation devices. First, the present fracture fixation device is economical, with less demanding technique, less blood loss, smaller incision, shorter surgical time, rapid mobilization, and most importantly includes a compression property. The fracture fixation device is adjustable in both length and rotation to avoid shortening and deformity of the fractured bone. The fracture fixation device further provides stable fixation to mobilize the patient for walking. In addition, the fracture fixation device may be applied under local anesthesia, leading to less morbidity and mortality post-operatively. Lastly, the fracture fixation device may be applicable on both right and left sides of the patient.

Thus, the invention provides fracture fixation devices, and methods for treating a bone fracture in a patient. More specifically, the present invention provides an external fracture fixation device for intertrochanteric fractures.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A fracture fixation device for treatment of a bone fracture, the fracture fixation device comprising:
    a main body having a recess formed therein;
    a compression element configured to be received in the recess, the compression element having a passage dimensioned to receive a fracture fixation pin,
    wherein the compression element is positioned such that a first side of the compression element faces the bone fracture and a second side of the compression element faces the main body, and wherein when the fracture fixation pin is received in the compression element and into a bone having the bone fracture, a compressive force is generated across the bone fracture to promote healing of the bone fracture,
    wherein the compression element includes an opening substantially parallel to the passage, the opening dimensioned to receive a compression adjustment screw for adjusting the compressive force generated across the bone fracture, and
    wherein the compression adjustment screw includes external threads configured to engage internal threads of the opening, wherein upon rotation of the compression adjustment screw, the compression element translates within the recess of the main body.

2. The fracture fixation device of claim 1, wherein the recess is substantially oval in cross-section and the compression element includes an oval in cross-section shape dimensioned to be received by the substantially oval shaped recess.

3. The fracture fixation device of claim 1, wherein the main body and compression element are configured to remain external to a subject when the fracture fixation device is coupled to the subject during treatment of the bone fracture.

4. The fracture fixation device of claim 1, wherein the main body is constructed from a material including at least one of an aluminum alloy, a stainless steel material, a carbon fiber material and a compact plastic material, wherein the material is at least partially radiolucent.

5. The fracture fixation device of claim 1, wherein the compression element includes a guide channel extending through a peripheral portion of the compression element, the guide channel configured to receive a locking pin extending through a top portion of the main body to inhibit translation of the compression element within the recess.

6. The fracture fixation device of claim 1, wherein the main body includes;
    a first section including the recess and compression element; and
    a second section pivotally coupled to the first section by a first connection,
    wherein the first connection allows the first section and the second section to pivot relative to each other about a first axis, the first axis being transverse to the passage of the compression element.

7. The fracture fixation device of claim 6, the compression element further comprises an additional passage dimensioned to receive an additional fracture fixation pin, wherein the additional passage is substantially parallel to the passage.

8. The fracture fixation device of claim 7, wherein the fracture fixation pin and the additional fracture fixation pin are configured to be received by a femoral neck at a predetermined angle relative a femoral shaft and extend across a fracture line created by the bone fracture.

9. The fracture fixation device of claim 8, wherein the bone fracture includes an intertrochanteric hip fracture and the fracture line extends from a greater trochanter to a lesser trochanter of a femur.

10. The fracture fixation device of claim 8, wherein the predetermined angle is in a range of 110 degrees to 160 degrees and is adjustable by pivoting the first section about the first axis.

11. The fracture fixation device of claim 6, wherein the first connection is formed by a first connection bolt extending through the first section and the second section along the first axis.

12. The fracture fixation device of claim 6, wherein the main body further includes a third section coupled to the second section by a second connection, wherein the second connection allows the second section and the third section to pivot relative to each other about a second axis, the second axis being longitudinal to the passage of the compression element.

13. The fracture fixation device of claim 12, wherein the second connection further allows the second section and the third section to axially translate along the second axis to at least one of increase and decrease an overall length of the fracture fixation device.

14. The fracture fixation device of claim 12, wherein the second connection is formed by a substantially cylindrical pivot pin extending along the second axis, the pivot pin positioned substantially perpendicular to a first connection bolt.

15. The fracture fixation device of claim 14, wherein the main body further includes a fourth section coupled to the third section by a third connection, wherein the third connection allows the third section and the fourth section to pivot relative to each other about a third axis, the third axis being transverse to the passage of the compression element.

16. The fracture fixation device of claim 15, wherein at least one of the first connection, the second connection, and the third connection are adjustable to allow the fracture fixation device to be externally coupled to a bone of a subject.

17. The fracture fixation device of claim 15, wherein the third connection is formed by a third connection bolt extending through the third section and the fourth section along the third axis.

18. The fracture fixation device of claim 17, wherein the third connection bolt is positioned substantially perpendicular the pivot pin of the second connection.

19. The fracture fixation device of claim 15, wherein the main body further includes a fifth section releasably coupled to the fourth section, the fourth section and the fifth section being opposing sections dimensioned to create at least one opening configured to receive a bone fixation pin.

20. The fracture fixation device of claim 19, further comprising at least one clamping bolt extending through the fourth section and the fifth section, wherein upon rotation in a first direction of the at least one clamping bolt, the bone fixation pin is clamped within the at least one opening.

21. The fracture fixation device of claim 19, further comprising at least one additional opening created by the opposing fourth section and fifth section and configured to receive an additional bone fixation pin.

22. The fracture fixation device of claim 21, wherein a distance between the at least one opening and the at least one additional opening is between about 0.5 centimeters and about 2.5 centimeters.

23. The fracture fixation device of claim 21, wherein the bone fixation pin and the additional bone fixation pin are configured to be received by a femoral shaft.

24. A method for treatment of a bone fracture using a fracture fixation device, the method comprising:
(a) adjusting a compression element configured to be received in a recess formed in a main body, the compression element positioned such that a first side of the compression element faces the bone fracture and a second side of the compression element faces the main body;
(b) inserting a fracture fixation pin through a passage created within the compression element and into a bone containing the bone fracture;
(c) generating a compressive force across the bone fracture to promote healing of the bone fracture;
(d) inserting a compression adjustment screw into an opening of the compression element; and
(e) rotating the compression adjustment screw to translate the compression element within the recess of the main body, thereby adjusting the compressive force generated across the bone fracture.

25. The method of claim 24, further comprising the step of coupling the fracture fixation device external to a subject during treatment of the bone fracture.

26. The method of claim 24, further comprising the step of pivoting a first section relative to a second section of the main body about a first axis and fixating in a first position, the first axis being transverse to the passage of the compression element.

27. The method of claim 26, further comprising the steps of:
pivoting the second section relative to a third section of the main body about a second axis and fixating in a second position, the second axis being longitudinal to the passage of the compression element; and
translating the second section and the third section axially along the second axis to at least one of increase and decrease an overall length of the fracture fixation device.

28. The method of claim 27, further comprising the step of pivoting the third section relative to a fourth section of the main body about a third axis and fixating in a third position, the third axis being transverse to the passage of the compression element.

29. The method of claim 28, wherein pivoting sections of the main body about at least one of the first axis, the second axis, and the third axis and fixating in the first position, second position, and third position allow the fracture fixation device to be externally coupled to a bone of a subject.

* * * * *